(12) United States Patent
Detour

(10) Patent No.: US 6,176,868 B1
(45) Date of Patent: Jan. 23, 2001

(54) DEVICE FOR THE NON-INVASIVE SUTURELESS CLOSURE OF THE OPEN EDGES OF WOUND IN THE SKIN OF A MAMMAL

(76) Inventor: Didier Detour, 126bis rue de la République, 28300 Saint Prest (FR)

(*) Notice: Under 35 U.S.C. 154(b), the term of this patent shall be extended for 0 days.

(21) Appl. No.: 09/466,879

(22) Filed: Dec. 20, 1999

(30) Foreign Application Priority Data

Nov. 22, 1999 (FR) .................................................. 99 14632

(51) Int. Cl.$^7$ .................................................. A61B 17/08
(52) U.S. Cl. ........................................... 606/215; 606/216
(58) Field of Search ..................................... 606/213–216

(56) References Cited

U.S. PATENT DOCUMENTS

| | | | | |
|---|---|---|---|---|
| 345,541 | * | 7/1886 | Reichardt | 606/216 |
| 363,538 | * | 5/1887 | Penny | 606/215 |
| 1,774,489 | * | 8/1930 | Sarason | 606/216 |
| 2,196,296 | * | 4/1940 | Flynn | 606/216 |
| 3,983,878 | * | 10/1976 | Kawchitch | 606/167 |
| 4,526,173 | * | 7/1985 | Sheehan | 606/216 |
| 4,815,468 | * | 3/1989 | Annand | 606/216 |
| 4,825,866 | * | 5/1989 | Pierce | 606/216 |
| 5,665,108 | * | 9/1997 | Galindo | 606/215 |
| 6,033,429 | * | 3/2000 | Magovern | 606/216 |

* cited by examiner

Primary Examiner—Gary Jackson
(74) Attorney, Agent, or Firm—Clark & Brody

(57) ABSTRACT

The invention relates to a device for closing the open edges of a wound in the skin of a mammal, characterized in that it comprises:

a) at least one first elongated element comprising a first and a second end, said first end being intended to come into abutment on the skin near the first open edge of the wound, said second end being connected to first traction means which are provided, opposite the wound, to exert a traction to turn the first end towards the wound;

b) at least one second elongated element comprising a first and a second end, said first end being intended to come into abutment on the skin near the second open edge of the wound, and the second end being connected to second traction means which are provided, opposite the wound, to exert a traction to turn the first end towards the wound; and c) at least one connecting means is provided between said first and second elements to join the two elements together, said connecting means being disposed between said first and second ends of each first and second element in order to define a pivoting point of each first and second element.

This device allows a non-invasive, sutureless closure.

10 Claims, 1 Drawing Sheet

DEVICE FOR THE NON-INVASIVE SUTURELESS CLOSURE OF THE OPEN EDGES OF WOUND IN THE SKIN OF A MAMMAL

FIELD OF THE INVENTION

The present invention relates to a device for the non-invasive, sutureless closure of the open edges of a wound in the skin of a mammal, such as an animal or a human being, and for maintaining the open edges of the wound against one another, as well as the subcutaneous tissues, thus promoting the healing process with aeration at the level of the wound. The invention allows a tight closure of the skin, without traversing it, while allowing an aeration of the wound, i.e. the device according to the invention does not cover the wound.

Various devices for treating a traumatic or surgical wound are well known to the person skilled in the art, each device presenting advantages and drawbacks, either in terms of long-term aesthetic result or in the implementation time or in comfort, i.e. in terms of pain felt by the patient during the period of scarring or when the device in question is being placed in position or removed.

The most simple device is a yarn which sews together the open edges of the wound to ensure cohesion of the superficial layers. However, this property of cohesion is offered to a lesser degree at the level of the deep layers of the skin. It presents the drawback, on traversing the skin, of creating pain and scarring. The so-called Blair-Donati technique solves the problem of the faulty approximation of the deep layers of the skin, thus creating more pain and subsequent scarring, with the result that the period of healing of the wound is increased.

A technique of intradermic oversew is also known, which offers a better superficial scarring but which does not retain the subcutaneous tissues sufficiently, hence a subsequent widening of the scar. The drawback of this technique is that of necessitating a longer procedure which is very difficult to carry out.

The clip system is also known, of which various models exist, presenting the advantage of being very quick to install, but maintaining the drawback of a foreign body within the different structures of the skin, and of traversing the skin and therefore generating subsequent scars.

The use of adhesive tape, of the "sticking plaster" type, is also known, which presents an adhesive-less area at the level of the wound to retain the two edges of the wound in approximated position without touching the wound. A similar device is described in U.S. Pat. No. 5,665,108, but the major drawback of the adhesive tapes solutions is that aeration is very limited at the level of the wound, this generating fermentation processes which prevent healing.

U.S. Pat. No. 4,815,468 proposes a sutureless closure device for drawing together and closing the open edges of a wound while retaining them firmly in place, based on an inverted V spring system, the ends of the V presenting base plates cooperating with an adhesive tape. By drawing the arms of the V together, this inverted V system makes it possible to bring the open edges of the wound in contact with each other. However, this system presents the major drawback of preventing any aeration at the level of the wound.

It is a principal object of the present invention to solve the novel technical problem of providing a device for the non-invasive, sutureless closure of the open edges of a wound in the skin, while ensuring forces of cohesion of the subcutaneous tissues for a sufficiently long period to obtain joining thereof, allowing a long-term scarring of better quality to be obtained.

It is another object of the invention to solve the new technical problem set forth above by a solution which conserves the possibility of care, asepsis, visual inspection and aeration at the level of the wound during the scarring phase.

Another object of the invention is to solve the new technical problems set forth above by a solution which presents the advantage of not employing a foreign body within the integuments, thus limiting the risk of infection.

It is a further object of the invention to solve the new technical problems set forth above by a solution which is particularly simple, which requires only a minimum of components constituting the device, and which is particularly easy for any user without particular training to employ, thus making it accessible to every home, and also at a low cost price.

All the technical problems set forth hereinabove are simultaneously solved for the first time by the present invention, in particularly simple manner and at a low cost.

SUMMARY OF THE INVENTION

The present invention thus relates to a device for closing the open edges of a wound in the skin of a mammal, such as an animal or a human being, without suture, which retains the edges of the wound against each other, promoting the healing process, characterized in that it comprises:
  a) at least one first elongated element comprising a first and a second end, said first end being intended to come into abutment on the skin near a first open edge of the wound, said second end being connected to first traction means which are provided, opposite the wound, to exert a traction to turn the first end towards the wound;
  b) at least one second elongated element comprising a first and a second end, said first end being intended to come into abutment on the skin near the second open edge of the wound, and the second end being connected to second traction means which are provided, opposite the wound, to exert a traction to turn the first end towards the wound; and
  c) at least one connecting means is provided between said first and second elements to join the two elements together, said connecting means being disposed between said first and second ends of each first and second element in order to define a pivoting point of each first and second element.

The connecting means is advantageously made of a substantially non-extensible material.

According to an advantageous embodiment of the invention, the first end of each element presents a sufficient surface to exert a minimum pin-point compression on the skin.

According to another advantageous embodiment of the invention, the traction means comprise adhesive means connected to the second end, intended to adhere to a healthy area of the skin at a predetermined distance from the wound.

According to another advantageous embodiment of the device according to the invention, said first element is substantially identical to said second element, thus facilitating the manufacturing procedure.

According to another advantageous embodiment of the invention, said first element and said second element present a lower part and an upper part, said connecting means being disposed substantially at the join between the lower part and the upper part.

According to a particular embodiment, the upper part progressively tapers up to said traction means.

According to a presently preferred embodiment, said connecting means comprises at least one yarn, preferably at least two yarns, of predetermined length to allow each first and second element to be disposed on either side of the wound. This yarn is advantageously made of a substantially inextensible material presenting a good mechanical strength, such as nylon or the like.

According to another advantageous embodiment of the invention, the first end of each of said first and second elements is made of a material ensuring adherence and respect of the skin near the edge of the wound, regrouping the energy of approximation transmitted to the latter, such as for example a hydrocolloidal material or a material performing the same finction.

If the open wound is very long, closure thereof is advantageously obtained with a plurality of devices disposed side by side.

In order to reduce the risk of tear, an aerated protective upper layer, for example of the "non-woven" type, may be provided.

It will be noted that, thanks to the invention which comprises a connecting means such as a yarn, it is easy to ensure mechanical connection between the first element and the second element of the device according to the invention disposed on either side of a wound, while ensuring passage of air and possibly of care agents or products which may be necessary in the course of the healing process, this fundamentally distinguishing the invention from the prior known devices.

BRIEF DESCRIPTION OF THE DRAWINGS

The invention will be more readily understood on reading the following description with reference to the accompanying drawings, in which.

DESCRIPTION OF PREFERRED EMBODIMENT

Figure 1:
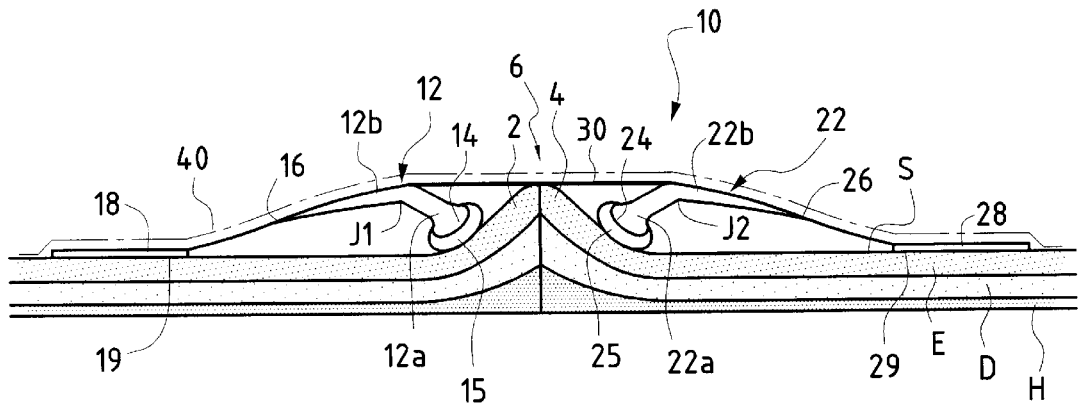
FIG. 1 is a perspective view in section illustrating a presently preferred embodiment of a sutureless device according to the present invention in position of operation, with the open edges of a wound in approximated position, with approximation of the subjacent tissues including the dermis and hypodermis.

Referring now to the drawings, a device according to the invention is represented by general reference number 10. This device 10 allows the non-invasive, sutureless closure of the edges 2, 4 of a wound 6 made in the epidermis E and also passing through the dermis D and the hypodermis H, the surface S of the epidermis commonly being called the skin.

Figure 2:
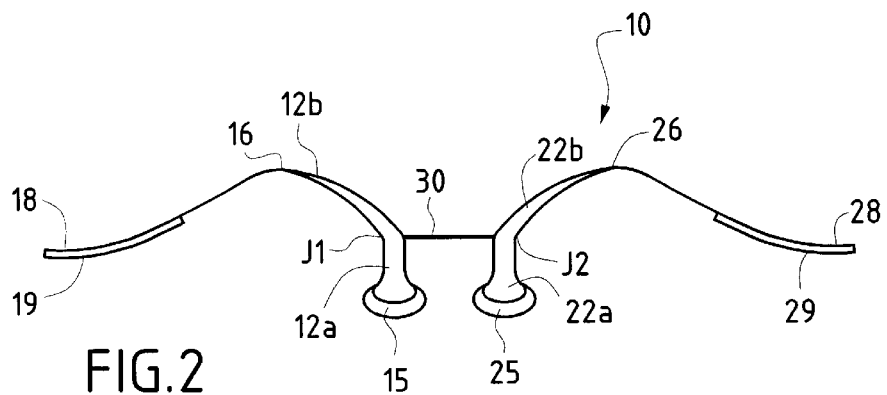
FIG. 2 shows the device according to the invention before being used.

The device 10 according to the invention comprises:

a) at least one first elongated element 12 comprising a first end 14 and a second end 16. The first end 14 is intended to come into abutment on the skin S near the first open edge 2 of a wound 6, and the second end 16 being connected to first traction means 18 which are located opposite the wound 6, as is visible in FIG. 1, to exert a traction to turn the first end 14 towards the wound 6, as the person skilled in the art will readily understand when considering FIGS. 1 and 2;

b) at least one second elongated element 22 also comprising a first end 24 and a second end 26, said first end 24 also being intended to come into abutment on the skin S near the second open edge 4 of the wound 6, said second end 26 being connected to second traction means 28 which are located opposite the wound 6 and provided to exert a traction to turn the first end 24 towards the wound 6, as the person skilled in the art will readily understand when considering FIGS. 1 and 2; and c) at least one connecting means 30 is provided between said first element 12 and second element 22 to join the two elements 12 and 22 together, said connecting means 30 being disposed between said first ends 14, 24 and second ends 16, 26 of each first (12) and second (22) element in order to define a pivoting point of each element 12, 22.

According to an advantageous embodiment of the invention, the first end 14, 24 respectively of each element presents a sufficient surface to exert a minimum pin-point compression on the skin S.

When the length of the wound 6 is great, the wound 6 is advantageously closed by a plurality of devices 10 disposed side by side.

According to another advantageous embodiment of the invention, the traction means 18, 28 comprise adhesive means, for example an adhesive tape 19, 29, of conventional type, connected to the second end 16, 26, respecitvely and intended to adhere to a healthy area of the skin at a predetermined distance from the wound 6, as is readily understandable from FIG. 1.

According to another advantageous embodiment of the invention, the first element 12 and the second element 22 are substantially identical, or identical.

According to a particular embodiment of the invention, the first element 12 and the second element 22 present a lower part 12*a*, 22*a* respectively and an upper part 12*b*, 22*b* respectively, said connecting means 30 being disposed substantially at the zone of join J1, J2 respectively between the respective lower part 12*a*, 22*a* and the respective upper part 12*b*, 22*b*.

According to an advantageous variant embodiment, the upper part 12*b*, 22*b* of each element 12, 22 tapers progressively up to join with the traction means 18, 28, respectively.

Figure 3:
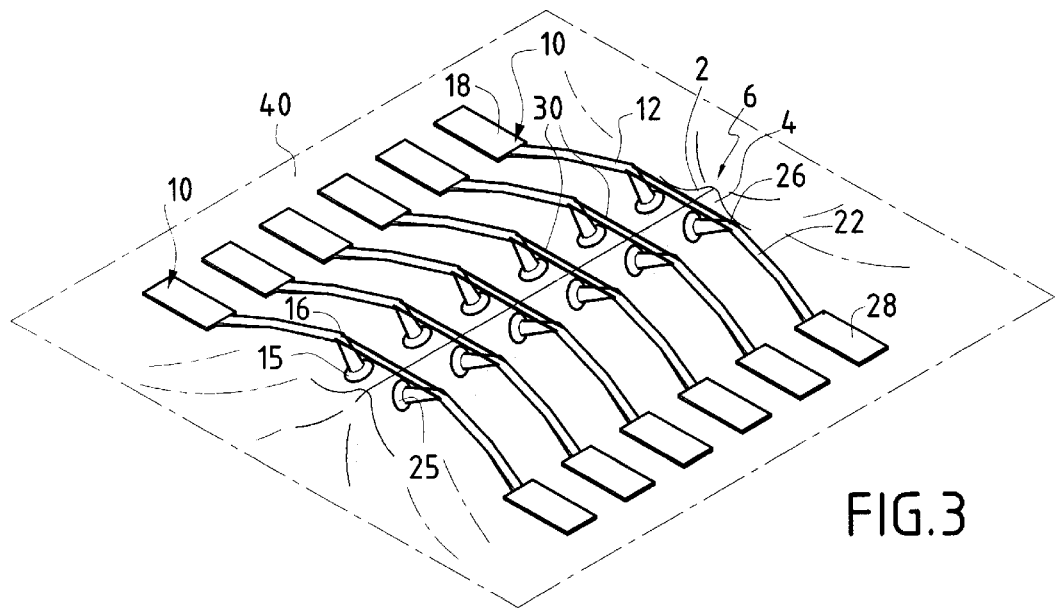
FIG. 3 shows a perspective view of a plurality of devices according to the invention, disposed in position of operation to close a wound of a certain length, for the non-invasive, sutureless closure according to the invention, the devices being covered with an aerated, non-woven protective device.

According to a presently preferred embodiment, each connecting means 30 comprises at least one yarn, preferably at least two yarns, as shown in FIG. 3, of predetermined length to allow each first element 12 and second element 22 to be disposed on either side of the wound 6, while ensuring a sure and reliable mechanical connection for producing an effect of pressure and turning of the skin and the subcutaneous tissues, including the epidermis, the dermis and the hypodermis, as shown in FIG. 1, these various tissues being retained side by side in order to close the wound 6 completely, as shown in FIG. 1.

It will be understood that the invention provides a device which comprises an element 12, 22, respectively, exerting a lever effect allowing the transmission of energy of cohesion necessary for the wound 6 to scar. The device according to the invention, via the first element 12 and second element 22, can transmit to the lower layers of the skin, in particular the dermis and the hypodermis, an increase in pressure added to the traction exerted by the respective traction means 18, 28.

It will thus be understood that the invention allows closure of the open edges of a wound without suture and in non-invasive manner, while allowing aeration of the wound which promotes the healing process.

The first end 14, 24 respectively of each respective element 12, 22 is advantageously provided with an adhesive element 15, 25 respectively for firmly connecting the respective first end 14, 24 to the skin S near the first edge 2 or second edge 4 of the wound 6, to ensure a sure and reliable anchoring of this end in position.

It will be readily understood that the device according to the invention is particularly simple and easy to place in position.

The adhesive element 15 of the first end 14 of the first element 12 is firstly adhered on the first edge 2 of the wound 6, then the adhesive element 25 of the first end 24 of the second element 22 is adhered on the skin S at the level of the second edge 4 of the wound 6.

A traction is then exerted either simultaneously or successively on the first traction means 18 and the second traction means 28 until the open edges 2, 4 of the wound 6 come into complete contact against one another and the traction means 18, 28 are then applied, thanks to their adhesive element, on the skin S in an appropriate area of the skin enabling the open edges 2, 4 of the wound 6 to be maintained in contact against each other, as shown in FIG. 1.

The wound 6 is generally of a certain length which necessitates the application of a plurality of devices 10 according to the invention, spaced from one another at a distance to be estimated by the practitioner, so as to ensure a sure and reliable, sutureless, non-invasive closure, as shown in FIG. 3.

In order to reduce the risk of tear, a device 40 forming an upper, aerated protective layer, for example of the "non-woven" type, such as non-woven aerated gauze, well known to practitioners, may be provided.

It will be readily understood that, thanks to the connecting means 30, the invention makes it possible mechanically to connect the first element 12 and the second element 22, and, by positioning the connecting means on the zone of join J1 or J2 of the first element 12 and of the second element 22, to ensure an effect of pressure and of approximation not only of the epidermis but also of the dermis and hypodermis until the edges 2, 4 of the open wound are in contact against each other as shown in FIG. 1.

The device according to the invention is preferably used once only.

The dimensions and the materials for making the device according to the invention are within the scope of the person skilled in the art who will have no difficulty in choosing them.

In a preferred embodiment, each first element 12 and second element 22 is made of light, non-allergic plastics material such as nylon, polyethylene, or mineral such as graphite and presents at its ends 12a, 22a a dimension generally included between 3 and 6 mm. The length of the yarns 30, also made of nylon for example, will generally also be included between 3 and 5 mm, the diameter of the nylon yarns not being critical, but must be sufficient to provide sure and reliable mechanical strength. This diameter may for example be from 0.1 to 1 mm. The yarn 30 is connected to each element 12, 22 at a distance of the order of 3 to 4 mm from the base constituted by the adhesive material 15 or 25. The adhesive element 15, 25 will be constituted by a block of hydrocolloidal material available on the market and well known to practitioners. The adhesive tapes 19, 29 are of the conventional type available on the market, for example adhesive strips of the Steristrip® type marketed by the firm 3M.

The protective layer 40 will be constituted by a non-woven aerated gauze available on the market.

What is claimed is:

1. Device for closing the open edges of a wound in the skin of a mammal, such as an animal or a human being, and retaining the edges of the wound against each other, promoting the healing process, wherein it comprises:

a) at least one first elongated element comprising a first and a second end, said first end being intended to come into abutment on the skin near the first open edge of the wound, said second end being connected to first traction means which are provided, opposite the wound, to exert a traction to turn the first end towards the wound;

b) at least one second elongated element comprising a first and a second end, said first end being intended to come into abutment on the skin near the second open edge of the wound, and the second end being connected to second traction means which are provided, opposite the wound, to exert a traction to turn the first end towards the wound; and c) at least one connecting means is provided between said first and second elements to join the two elements together, said connecting means being disposed between said first and second ends of each first and second element in order to define a pivoting point of each first and second element.

2. The device of claim 1, wherein the first end of each element presents a sufficient surface to exert a minimum pin-point compression on the skin.

3. The device of claim 1, wherein the open wound is considerably long and closure thereof is obtained by a plurality of devices disposed side by side.

4. The device of claim 1, wherein the traction means comprise adhesive means connected to the second end of each element, intended to adhere in a healthy zone of the skin at a predetermined distance from the wound.

5. The device of claim 1, wherein the first element and the second element are substantially identical.

6. The device of claim 1, wherein the first element and the second element present a lower part and an upper part, the connecting means being disposed substantially at the join between the lower part and the upper part.

7. The device of claim 6, wherein the upper part tapers progressively up to the traction means.

8. The device of claim 1, wherein the connecting means comprises at least one yarn, of predetermined length to allow each first element and second element to be disposed on each side of the wound.

9. The device of claim 1, wherein an aerated protective layer, for example of "non-woven" type, is provided, in order to reduce the risk of tear.

10. The device of claim 8, wherein the connecting means comprises at least two yarns of predetermined length to allow each first element and second element to be disposed on each side of the wound.

* * * * *